(12) United States Patent
Schipper et al.

(10) Patent No.: US 7,529,633 B1
(45) Date of Patent: May 5, 2009

(54) APPLICATION OF CARBON NANOTUBE HOLD-OFF VOLTAGE FOR DETERMINING GAS COMPOSITION

(75) Inventors: John F. Schipper, Palo Alto, CA (US); Jing Li, San Jose, CA (US)

(73) Assignee: The United States of America as represented by the National Aeronautics and Space Administration (NASA), Washington, DC (US)

( * ) Notice: Subject to any disclaimer, the term of this patent is extended or adjusted under 35 U.S.C. 154(b) by 443 days.

(21) Appl. No.: 11/203,589

(22) Filed: Aug. 5, 2005

(51) Int. Cl.
*G01N 33/00* (2006.01)
*G06F 17/00* (2006.01)

(52) U.S. Cl. .............................. 702/50; 702/22; 702/24; 702/30; 702/32; 977/839

(58) Field of Classification Search .................... 702/50, 702/22, 23, 24, 30, 32
See application file for complete search history.

(56) References Cited

U.S. PATENT DOCUMENTS 6,437,329 B1 * 8/2002 Yedur et al. ................. 250/306
7,276,266 B1 * 10/2007 Khare et al. ................ 427/533

2006/0251543 A1 * 11/2006 Koratkar et al. ............... 422/98

OTHER PUBLICATIONS

Zhang et al., "Study of gas sensor with carbon nanotube film on the substrate of porous silicon", Aug. 12-16, 2001, IEEE, Proceedings of the 14th Vacuum Microelectronics Conference, 2001. IVMC 2001, pp. 13-14.*

Suehiro, et al., Detection of partial discharge in SF6 gas using a carbon nanotube-based gas sensor, Sensors and Actuators B, 2005, 164-169, 105, Elsevier B. V.

* cited by examiner

*Primary Examiner*—Hal D Wachsman
(74) *Attorney, Agent, or Firm*—John F. Schipper; Robert M. Padilla

(57) ABSTRACT

Method and system for determining chemical composition of a single-component or multiple-component gas, using a discharge holdoff mechanism. A voltage difference V between two spaced apart electrodes is brought to a selected value and held, the holdoff time interval $\Delta t(V;ho)$ required before gas discharge occurs is measured, and the associated electrical current or cumulative electrical charge is measured. As the voltage difference V increases, the time interval length $\Delta t(V;ho)$ decreases monotonically. Particular voltage values, $V_\infty$ and $V_0$, correspond to initial appearance of discharge ($\Delta t \approx \infty$) and prompt discharge ($\Delta t \approx 0$). The values $V_\infty$ and $V_0$ and the rate of decrease of $\Delta t(V;ho)$ and/or the rate of increase of current or cumulative charge with increasing V are characteristic of one or more gas components present.

12 Claims, 6 Drawing Sheets

APPLICATION OF CARBON NANOTUBE HOLD-OFF VOLTAGE FOR DETERMINING GAS COMPOSITION

ORIGIN OF THE INVENTION

This invention was made by one or more employees of the U.S. government. The U.S. Government has the right to make, use and/or sell the invention described herein without payment of compensation therefor, including but not limited to payment of royalties.

FIELD OF THE INVENTION

This invention relates to use of variable voltages, applied to an exposed end of a carbon nanotube immersed in a gas mixture for a variable time interval, to estimate gas composition.

BACKGROUND OF THE INVENTION

Few sensors are available to detect inert gases. Conventional inert gas analysis tools primarily rely upon infrared (IR) spectroscopy, mass spectroscopy (MS) and/or thermal conductivity measurements. Thermal conductivity sensors are available for fixed and portable instruments, but this technique is not suitable for measuring extremely low levels of a gas (e.g., less than 1 percent by volume resolution), and the technique has difficulties when the target gas has a thermal conductivity close to that of a background gas. For example, measurement of oxygen in air is not feasible, because the two gases have essentially the same thermal conductivity.

IR spectroscopy is often used to measure carbon dioxide in air, or methane in carbon dioxide, as found in sewage digestor and coal gasification plants. This technique is superior to thermal conductivity sensing in accuracy and resolution, but use of IR is more expensive due to the complex optics and signal processing required. A MS-based sensor can be used to detect pressure of an inert gas, but this technique is expensive and heavy and time consuming and is not suitable for in situ measurements. Fourier transform IR and MS techniques require bulky, heavy instruments and/or high temperature operation, and consumption of electrical power is very large.

A voltage pulse discharge approach may provide a reasonable estimate of a threshold voltage for which discharge first occurs, and thus provide an estimate, by means of exclusion of most others, of a gas component having the smallest threshold discharge voltage. In practice, many workers do not distinguish between a discharge in a gas component that occurs instantaneously and a discharge in the same gas component that occurs only after a modest time delay (e.g., 5-30 sec) for what appears to be the same discharge. However, in some materials, the time delay decreases monotonically with increase in the pulse voltage so that the so-called discharge voltage may be ambiguous.

What is needed is a relatively lightweight and small sensor for inert gas components that consumes a relatively small amount of power, that provides measurements that are as accurate as the conventional approaches, and that distinguishes between a gas component discharge that occurs substantially instantaneously and a discharge in the same gas component that occurs after a substantial time delay. Preferably, this sensor should be able to detect and identify presence of one, two or more gas components, some or all of which may be relatively inert (e.g., Ne, Ar, Xe, Kr, CO, etc.), and to provide an estimate of concentration of at least one gas component

SUMMARY OF THE INVENTION

These needs are met by the invention, which provides a method and associated system to vary a voltage, applied to an exposed end of a carbon nanotube for a selected time interval, to promote gas discharge and to estimate a gas component involved in the discharge. Each component of a gas has a first (lower threshold discharge voltage value, $V_\infty$, at which discharge can occur after a long time delay ($\Delta t(V_\infty;ho) \approx \infty$), where "ho" refers to a discharge voltage holdoff value. Application of a voltage V above this lower limit $V_\infty$ will cause the gas component to undergo a discharge after a discharge holdoff time $\Delta t(V;ho)$ that decreases as V increases above $V_\infty$. When the voltage V is equal to or greater than a second (upper) prompt discharge voltage value $V_0$ ($V \geq V_0 \geq V_\infty$), the discharge occurs substantially instantaneously, as illustrated in FIG. 1; $\Delta t(V \geq V_0;ho) \approx 0$. For some gas components, it may occur that $V_\infty \approx V_0$ so that a substantially unique discharge voltage threshold exists; this may occur at low concentrations of that gas component. For other gas components, it may occur that $V_\infty < V_0$ and any voltage V in the range $V_\infty < V < V_0$ will produce a discharge after a certain discharge holdoff time delay $\Delta t(V;ho)$ (>0); in this instance, a single or unique discharge voltage does not exist.

This procedure can be used to distinguish between two or more components (k=1, 2, . . . , K) present in a gas, if the threshold discharge voltage values $V_\infty(k)$__ for each of the two or more gas components are spaced apart by at least a reasonable amount. As the voltage V is increased, the rate of change of an electrical parameter, such as current or cumulative electrical charge, will change (e.g., become non-zero) as the threshold discharge voltage value $V_\infty(k)$ of each distinct gas component is exceeded.

This invention should be useful, by itself or in combination with other gas discharge methods, to determine the gas or gases are present in a gaseous medium, at low or moderate concentrations, and to estimate the concentration of one or more of the gases present. This invention can be automated, if desired, and used in space exploration (e.g., in a planet or satellite fly-by or for a crew exploration vehicle). This invention can also be used in a terrestrial environment, such as determination of gas composition in a hazardous substance environment. Use of one or more carbon nanotube contacts may allow a more precise determination of discharge voltage holdoff than would be available where a larger diameter electrical contact is used.

DESCRIPTION OF BEST MODES OF THE INVENTION

Figure 2:
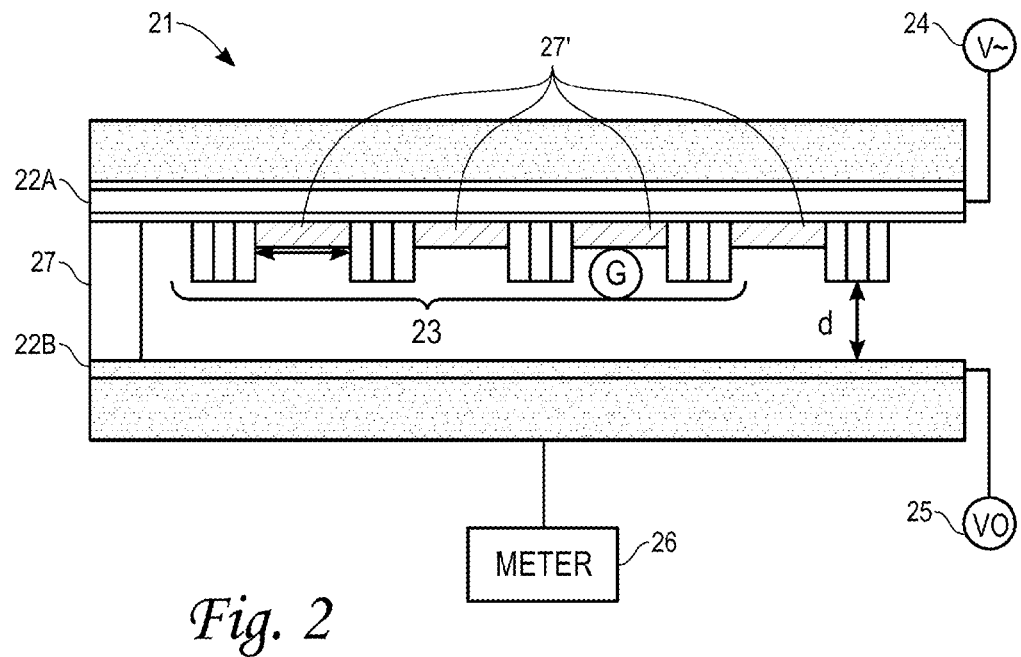
FIGS. 2 and 4 schematically illustrate systems for practicing the invention.

In FIG. 2, a gas detection system 21 using one or more carbon nanotubes ("CNTs") 23 connected to a variable voltage plate 22A, as anode, is spaced apart (d≈10-200 μm) from a grounded or other constant-voltage plate 22B, as cathode. A gas G having an unknown composition and/or an unknown concentration is positioned in the anode-cathode gap. The variable voltage plate 22A is connected to a variable voltage source 24, and the constant voltage plate is maintained by a constant voltage source 25 (e.g., ground). An electrical current I(V) and/or a cumulative electrical charge e(V) is measured, as a function of the voltage difference V (maintained for an unlimited time) above $V_\infty(n)$ for one or more indices n=1, 2, ..., by an ammeter or cumulative electrical charge meter 26 (collectively referred to as a "meter" herein). Electrically insulating spacers 27 and/or 27' are optionally positioned between adjacent electrically charged system components.

A voltage (difference) V is increased in steps and held approximately constant at each of a discrete sequence of voltages until a gas discharge first occurs after a holdoff (ho) time interval $\Delta t(V_\infty;ho)$ after a threshold discharge voltage $V_\infty$ is established. Theoretically $\Delta t(V_\infty;ho) \approx \infty$. The voltage V is used to determine information on at least one gas component and/or on gas concentration in the gap, for one, two or more gas components.

Figure 1:
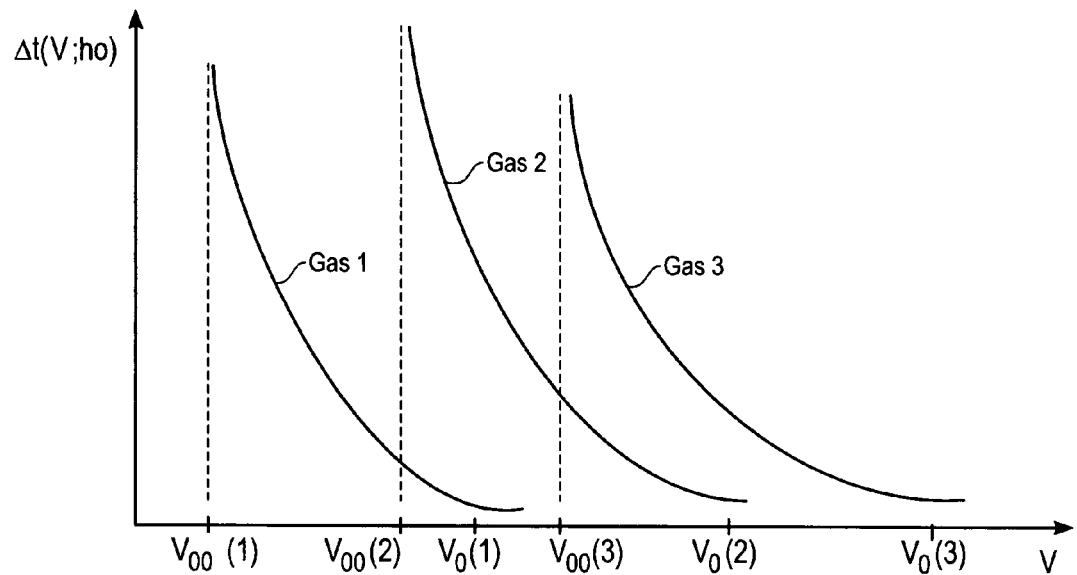
FIGS. 1, 6 and 7 graphically illustrate variation of a discharge hold off time $\Delta t(V;ho)$ with variation of an applied voltage V for several gas component (FIG. 1) and for a single gas component (FIGS. 6 and 7).
Figure 3:
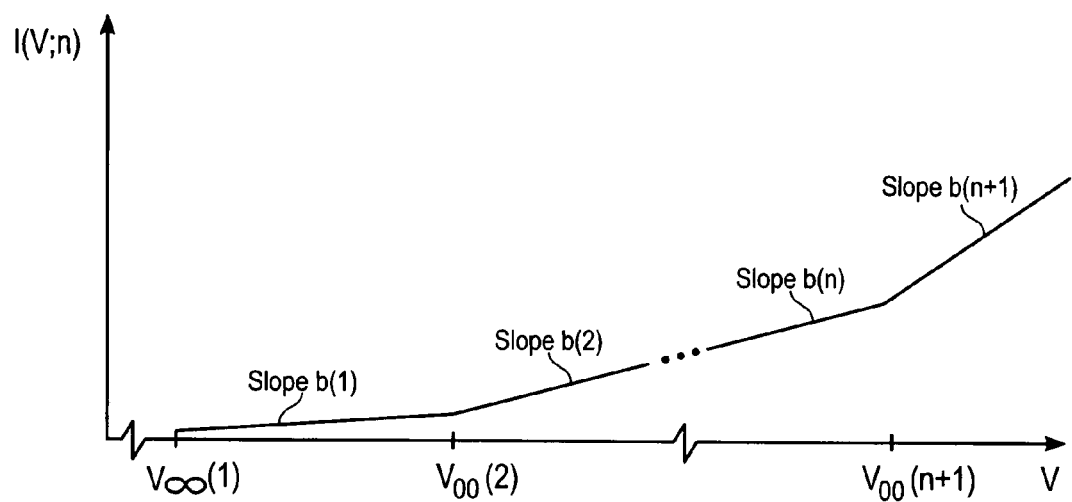
FIG. 3 graphically illustrates variation of a measurable electrical parameter with applied voltage V where two or more gas components are present.

The voltage difference $\Delta V$ is further increased above the threshold $V_\infty$, preferably in discrete steps, until a gas discharge occurs within a time interval of selected length (e.g., within 30 sec) after the (constant) voltage is established. This discharge holdoff voltage will increase from a lowest value $V_\infty$, which will require a very long time (theoretically, an infinite time) for discharge to occur, to higher voltages, $V=V_i>V_\infty$, where the discharge hold-off time $\Delta t(V;ho)$ is finite and decreases monotonically with increasing voltage V, as illustrated in FIG. 1. For a single gas component present in the gap, one or more of the pairs of values $\{(V, \Delta t(V;ho))\}_V$ will be characteristic of the gas and can potentially distinguish more accurately between gas components than does a pulsed voltage, which ignores the time required for a discharge to occur and implicitly assumes that $V_\infty=V_0$.

Where $N(\geq 2)$ gas components with distinct hold-off voltages, $V_\infty(n)$ and $V_\infty(n+1)$ $(>V_\infty(n))$, are present in the gap, the first (lowest) threshold discharge voltage $V_\infty(1)$ is identified and the voltage V is increased in steps (discretely) until $V_\infty(2)$ is reached. In the range $V_\infty(n)<V<V_\infty(n+1)$, with n=1, 2, ..., N–1, the current will increase monotonically and approximately linearly with a characteristic slope b(n) until the (n+1)th threshold discharge voltage is reached, after which the measured current will increase approximately linearly (with a characteristic slope b(n+1)>b(n)) above $V_\infty(n+1)$, as illustrated in FIG. 3. The higher slope b(n+1) reflects the presence of parallel or additional discharge paths using the nth and (n+1)th gas components for $V>V_\infty(n+1)$. This change in slope at $V=V_\infty(n+1)$ plus the slope values, b(n) and b(n+1), can be used to characterize one, two or more gas components present, and possibly the (relative) concentrations of the component(s).

Use of constant (non-pulsed) holdoff voltages, rather than pulse voltages, to characterize the components and/or concentrations, of a gas present in an anode-cathode gap defined in part by exposed ends of one or more CNTs, allows use of the threshold parameters $V_\infty(n)$, the present slope value b(n), the current I(V) and/or cumulative electrical charge e(V) in the range $V_\infty(n) \leq V < V_\infty(n+1)$ to characterize one or more of the gas components and/or to provide consistency checks on the measurements. By contrast, use of a pulsed voltage discharge approach allows use of a lowest discharge pulse voltage V(disch;min) (assumed to be unique) and, with some ambiguity, the transient current I(V;n) or cumulative electrical charge e(V;n) associated with the condition $V \geq V(\text{disch;min})$.

Preferably, the slope b(n) of electrical current or cumulative electrical charge between any two consecutive holdoff voltages, $V_\infty(n)<V<V_\infty(n+1)$, is determined experimentally for the contribution of two gas constituents (numbers n and n+1) corresponding to these holdoff voltages. In this range, the electrical current I(V;n) (and, similarly, the cumulative electrical charge e(V;n)) may be expressed approximately as $$I(V;n)=I\{V_\infty(n);n\}b(n)\cdot\{V-V_\infty(n)\}^p(V_\infty(n)<V<V_\infty(n+1)), \quad (1)$$

with a choice $p=p(n) \approx 1$, illustrated graphically in FIG. 3. Within a small neighborhood surrounding voltage $V_\infty(n)$ the value of the associated current I(V) may be ambiguous or difficult to determine reasonably precisely. However, in an intermediate portion of this voltage range, such as $V \approx \{V_\infty(n)+V_\infty(n+1)\}/2$, the present slope b(n) can be determined reasonably accurately. The transition current value at $V=V_\infty(n+1)$ is then determined, graphically or numerically, by extending the approximately linear electrical current measurements for I(V;n) and I(V;n+1) until the two curves meet, $$I(V;n)=I(V;n+1) \text{ at } V_{V_\infty}(n+1), \quad (2)$$

which provides an estimate for the threshold discharge voltage value $V_\infty(n+1)$ and the corresponding initial current value $I(V=V_\infty(n+1);n+1)$. The approach associated with Eq. (2) can also be used where the current in an intermediate voltage range is nonlinear in V, for example, $$I(V;n)=I(V=V_\infty(n);n)+b(n)\cdot|V-V_\infty(n)|^{q(n)}(V_\infty(n) \leq V < V_\infty(n+1)), \quad (3)$$

where q(n) is an exponent having any positive value, which may vary with the index n. Analogs of Eqs. (1)-(3) may also be applied to a measure of cumulative electrical charge e(V;n) for $V_\infty(n) \leq V < V_\infty(n+1)$.

The threshold discharge voltage value $V_\infty(n)$ for a single gas component may vary with concentration c(n) of the component no. n. Where only a single component is present in the gas G, $V_\infty$ may vary with concentration c(n), because a mean scattering distance for gas particles (proportional to nearest neighbor distance) will be approximately proportional to $c(n)^{-1/3}$.

Figure 4:
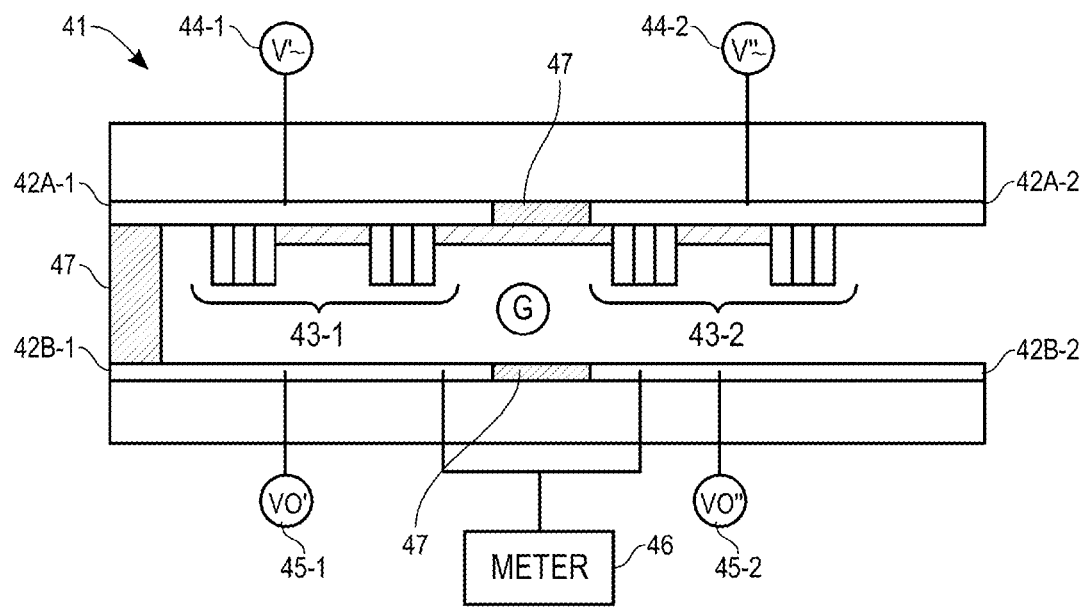

The system 41 shown schematically in FIG. 4 is similar to the system 21 in FIG. 2, with the following changes. The variable voltage plate 22A (in FIG. 2) is replaced by split voltage plates, 42A-1 and 42A-2; the constant voltage plate 22B is optionally replaced by split constant voltage plates, 42B-1 and 42B-2, having the same or different constant voltages sources, 45-1 (V0') and 45-2 (V0"); a different group of CNTs, 43-1 and 43-2, is connected to the respective plates, 42A-1 and 42A-2; the variable voltage plate 24 is replaced by independently controlled variable voltage plates, 44-1 and 44-2; and the meter 26 is optionally replaced by meters, 46-1 and 46-2, connected to the respective plates 42B-1 and 42B-2 (or to the respective plates 42A-1 and 42A-2). The system 41 allows substantially simultaneous use of two or more distinct voltages, V' and V", to interrogate the gas G, potentially increasing the operating efficiency of the system.

Figure 5A:
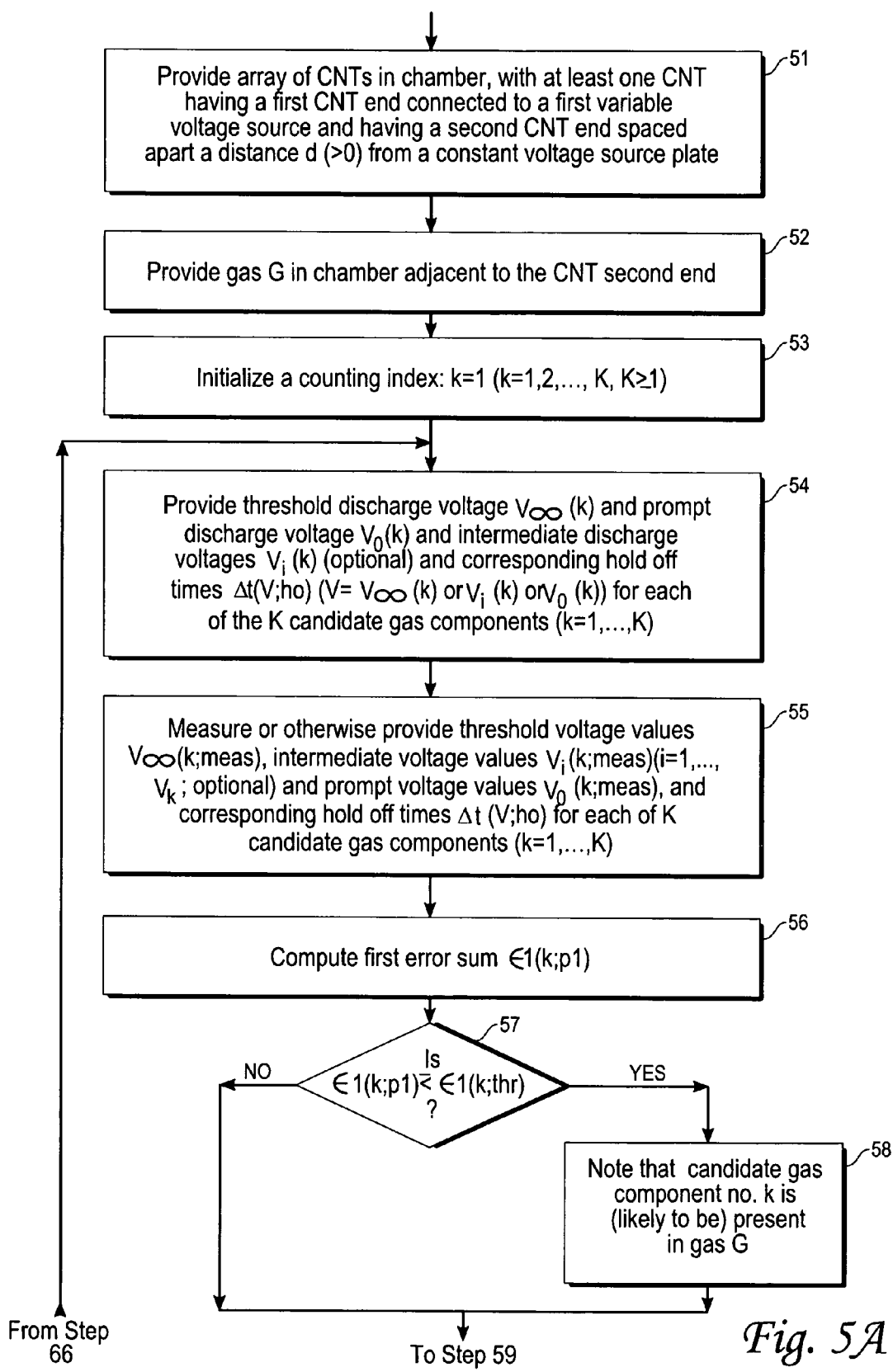
FIGS. 5A and 5B are a flow chart for practicing the invention.
Figure 5B:
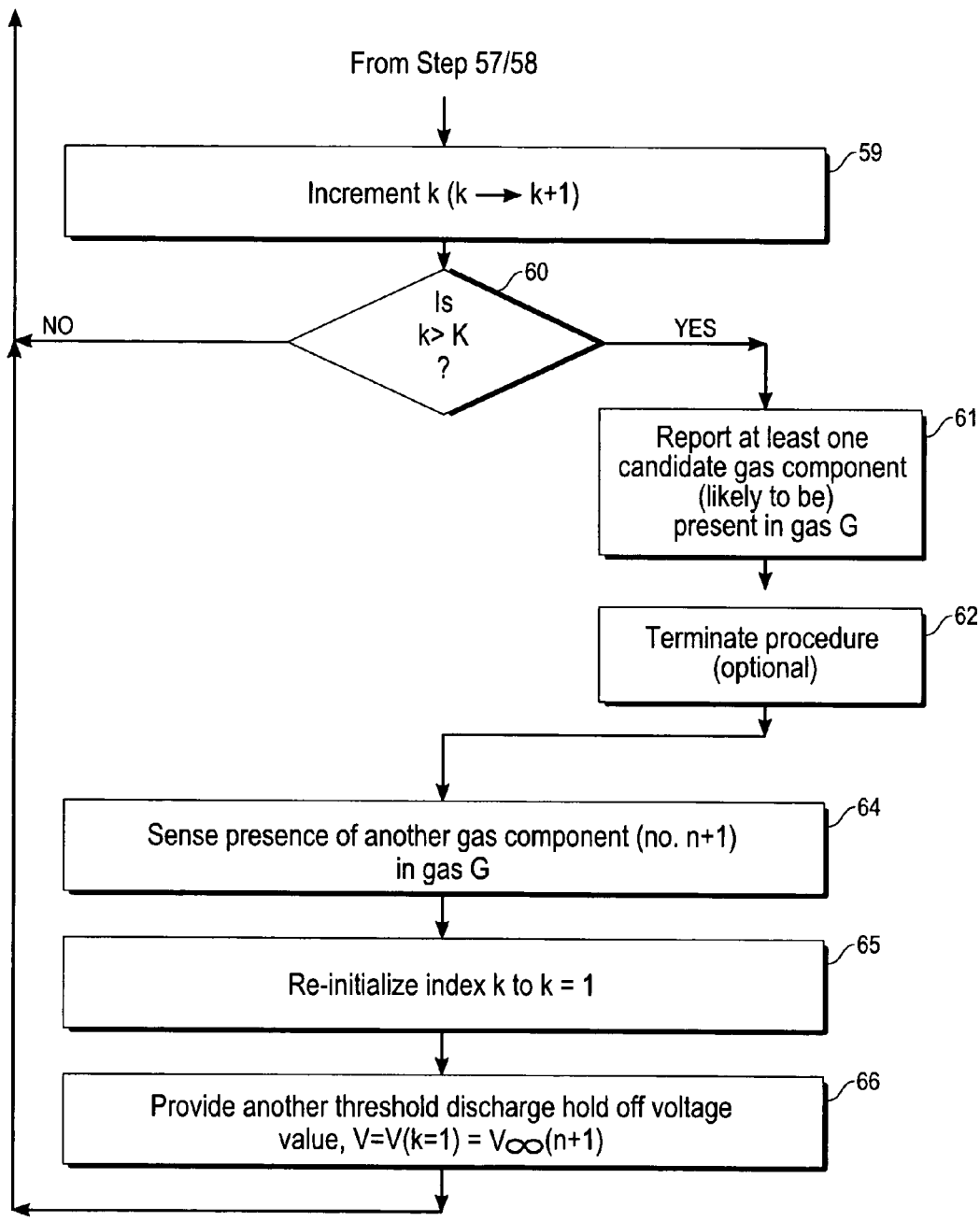

FIGS. 5A and 5B are a flow chart illustrating a basic procedure for practicing the invention. In step 51, a first array of spaced apart carbon nanotubes (CNTs) is provided in a closed chamber, at least one CNT in the first array being attached at a first CNT end to a first variable voltage source and having a relatively sharp CNT tip at a second end of the at least one CNT, where the second end of the at least one CNT in the first array is spaced apart a distance d in a range 10-200 μm from a substantially constant voltage plate. Each CNT array preferably has a diameter of at least 20 μm, more preferably lying in a range of 20-50 μm. The array diameter may be as small as 1-5 μm, or smaller if desired. Any two CNT arrays are preferably spaced apart by a distance of at least 200 μm, more preferably at least 500 μm. In step 52, a gas G, having at least one unknown gas component and having a pressure in a range $10^{-3}$–760 Torr, is provided in the chamber, adjacent to the CNT second end. In step 53, a counting index k (=1, ... , K; K≧2) is initialized to k=1, where K is the estimated number of candidate components in the gas G; identified, for example, by use of a slope change method such as illustrated in FIG. 3. In step 54, a collection of (known or estimated) threshold discharge voltage values $V_\infty(k)$, (known or estimated) intermediate discharge voltage values $V_i(k)$ (i=1, ... , $I_k$;$I_k$≧0), and (known or estimated) prompt discharge voltage values $V_0(k)$, and the corresponding discharge holdoff times $\Delta t(V;ho)$ ($V=V_\infty(k)$ or $V_i(k)$ (i=0, ... , $I_k$) or $V_0(k)$) are provided for each of the K candidate gas components.

In step 55, a threshold discharge voltage value $V_\infty(meas)$, a corresponding prompt discharge voltage value $V_0(meas)$, intermediate discharge voltage values $V=V_i(meas)$ (i=1, ..., $I_k$; optional), with $V_\infty(meas) \leq V_1(meas) \leq V_2(meas) \leq \ldots \leq V_0(meas)$, and corresponding observed discharge holdoff times $\Delta t(V;ho)$ are measured or otherwise provided for the gas G. In step 56, a first error sum of weighted magnitudes of difference values, for example.

$$\varepsilon 1(k; p1) = \sum_{i=0}^{I_k} w_i |V_i(k) - V_i(meas)|^{p1} + w_\infty |V_\infty(k) - V_\infty(meas)|^{p1}, \quad (4)$$

is computed, where $w_i$ and $w_\infty$ are non-negative weight coefficients and p1=p1(k) is a selected positive exponent number.

The system, in step 57, determines if $\varepsilon 1(k;p1)$ is no greater than a threshold error number $\varepsilon 1(k;thr)$, which may depend upon the index value k. If the answer to the query in step 57 is "yes," the system notes, in step 58, that the candidate gas component number k is (likely to be) present in the gas G, and moves to step 59, where the counting index k is incremented (k—>k+1). If the answer to the query is step 57 is "no," the system moves directly to step 59.

In step 60, the system determines if the (incremented) index k is greater than the number K of candidate gas components. If the answer to the query in step 60 is "no," the system returns to step 54, and steps 54-60 are repeated. If the answer to the query in step 60 is "yes," the system optionally reports that at least one of the candidate gas components, whose presence in the gas G was noted in step 58, is (likely to be) present in the gas G, in step 61. The process is optionally terminated in step 62.

One can ignore the effect(s) of the intermediate discharge voltage values in the error parameter $\varepsilon 1(k;p)$ in Eq. (4) by focusing on only the end values, $V_\infty(k)$ and $V_0(k)$ and/or by setting $w_i=0$ (i=1, ... , $I_k$).

In an alternative approach, a second error sum can be formed from weighted magnitudes of differences of the discharge holdoff times $$\varepsilon 2(k; p2) = \sum_{i=0}^{I_k} w_i |\Delta t(V_i(k); ho) - \Delta t(V_i(meas); ho)|^{p2}, \quad (5)$$

is computed, and the error sums $\varepsilon 1(k;p1(k))$ and $\varepsilon 1(k)$ are replaced by $\varepsilon 2(k;p2(k))$ and $\varepsilon 2(k)$, respectively, in steps 76 and 77, and a modified flow chart procedure is followed.

Where another (unknown) gas component number k+1, with k≧1) is present, or believed to be present, in the gas G, with $V_\infty(k+1) > V_\infty(k)$, the procedure is preferably not terminated in step 62. Presence of the component number k+1 may be sensed by identifying a new threshold discharge voltage value, $V=V_\infty(k+1)$ at which the slope b(k) in FIG. 3 changes substantially to a new slope, b(k+1)>b(k)), according to Eq. (3), in step 64. In step 65, the index k is re-initialized (to k=1). In step 66, another threshold discharge holdoff voltage, having a known value $V=V(k=1) \geq V_\infty(k+1)$ is provided, and steps 54-62 are reapplied to estimate or identify a (k+1)th component of the gas G.

Figure 6:
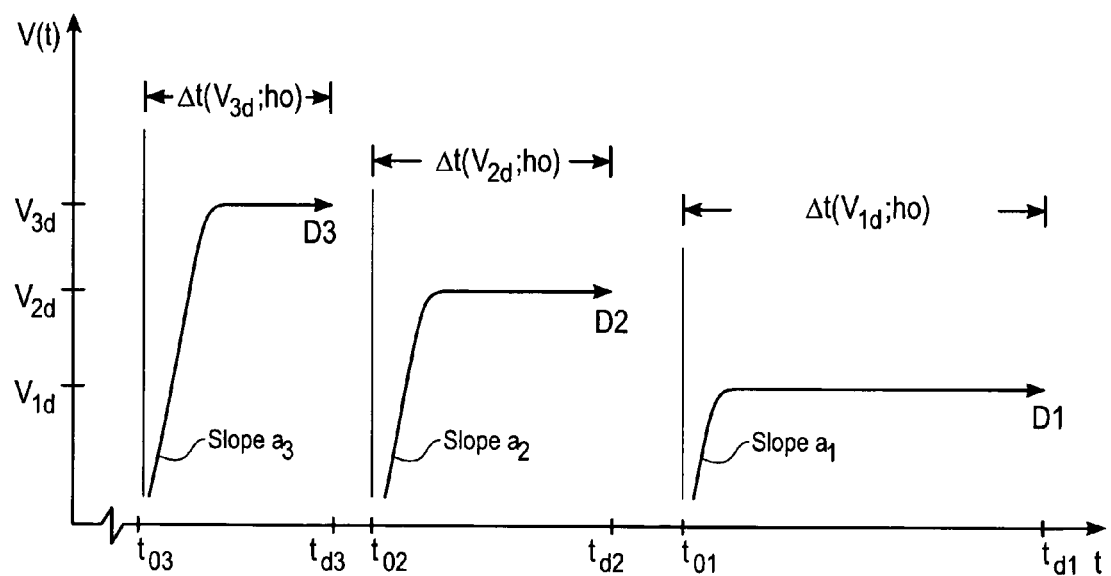

As an alternative approach to applying a step function voltage V (above $V_\infty$) and subsequently holding the voltage constant, the voltage V=V(t) may be increased (linearly or nonlinearly) with time t at selected rates of increase, from an initial value $V(t_{0n}) \approx 0$ to a value $V=V_{id} > V_\infty$ (i=1, 2, ... ) until the discharge occurs, for each of a sequence of initial times $t=t_{01} < t_{02} < t_{03} < \ldots$ This approach is illustrated in FIG. 6, where a voltage V(t) increases from $V(t_{0n}) \approx 0$ to a voltage $V=V_D V_i$ (k) at a discharge time, $t=t_{Di}$, where discharge occurs. Assuming that the initial slope $a_k = dV(t;k)/dt$ is large enough, the time difference $\Delta t = t_{Di} - t_{0i}$, which increases as $V_{id}$ decreases, should be substantially equal to the discharge holdoff time $\Delta t(V_{id};ho)$. The step function or square wave voltage forcing function used or assumed in connection with FIGS. 1, 2, 3, 4, 5A and 5B can be replaced by a more flexible monotonic voltage forcing function, such as illustrated in FIG. 6.

Figure 7:
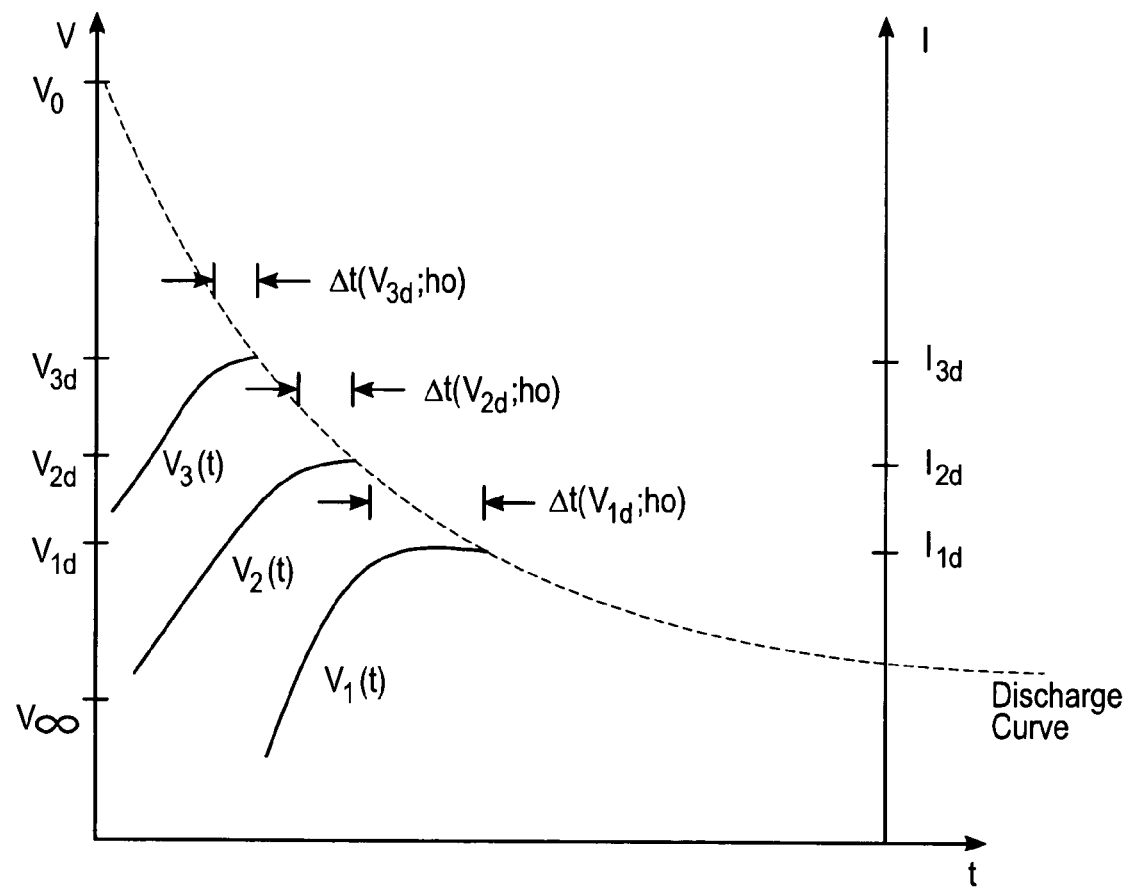

FIG. 7 illustrates effects of voltage ramp-ups, $V=V_i(t)$ (i=1, 2, 3) to different discharge voltages, $V=V_{id}$, corresponding discharge holdoff times, $\Delta t(V_{id};ho)$, and corresponding discharge currents, $I=I_{id}$, for a representative gas component. As $V_{id}$ increases, $\Delta t(V_{id};ho)$ decreases and $I_{id}$ increases monotonically, but not necessarily strictly monotonically.

Where another (unknown) gas component is present, or believed to be present, in the gas G, with a measured value V(new;meas;thr)>V(meas;thr), the procedure is preferably not terminated in step 62 in FIG. 5B. Presence of the new component may be sensed by determining a new threshold voltage discharge voltage value V=V(new;meas;thr), for example, at which the slope b(n) in FIGS. 3A/3B changes substantially to a new slope, b(k+1)>b(k), according to Eq. (3), in step 66 in FIG. 5B. The value V(meas;thr) is then replaced by the value V(new;meas;thr), and steps 54-66 in FIGS. 5A and 5B are reapplied to determine if another candidate gas component is likely to be present in the gas G.

The CNT-based gas sensor disclosed here uses the sharp (low radius of curvature) tip(s) of one or more CNTs, preferably multiwall carbon nanotubes ("MWCNTs") or carbon nanofibers ("CNFs"), to generate high strength electrical fields adjacent to the tip(s) for breakdown of gas components with lower voltage application and lower generation of high leakage current. The system and associated method can provide a high sensitivity, low power consumption tool that is very specific for identification of one or more gas components. A current meter can be multiplexed to measure the leakage current from each of two or more spaced apart CNT arrays, and the voltage delivered can be multiplexed to different CNT arrays to provide different discharge voltages to each array. The current measured in each sensing channel can be digitized to correlate with each of the components of a complex gas. The discharge gas sensor system disclosed here can identify one or more specific threshold discharge voltage values independently of the gas concentration.

The gas sensor disclosed here can be operated at room temperature, or at any other reasonable temperature, and at any reasonable pressure, such as atmospheric pressure or moderately lower. Where the gas pressure in the chamber is p and the tip-to-constant voltage plate distance is d, the product pd will approximately characterize the pulse breakdown threshold voltage where d is no more than 1-3 mean free paths at the gas concentration provided.

What is claimed is:

1. A method for estimating a component of a gas, the method comprising:
    (1) providing a first array of spaced apart carbon nanotubes (CNTs) in a chamber, at least one CNT in the first array being attached at a first CNT end to a first variable voltage source and having a relatively sharp CNT tip at a second CNT end of the at least one CNT, where the second CNT end of the at least one CNT in the first array is spaced apart a distance d, in a range of about 10-200 µm, from a substantially constant voltage plate;
    (2) providing a gas G, having at least one unknown gas component and having a pressure in a range of about $10^{-3}$–760 Torr, in the chamber;
    (3) identifying K candidate gas components, numbered k=1, . . . , K (K≧1) one or more of which may be present in the gas G;
    (4) providing a collection of pairs of estimated or known discharge voltage values and corresponding discharge holdoff times $\{V_j(k), \Delta t(V_j(k);ho)\}_j$ (j=0, 1, . . . , $I_k$, or j=∞), for the candidate gas component number k, where $V_\infty(k)$ is an estimated or known threshold discharge voltage value, $V_0(k)$ is an estimated or known prompt discharge voltage value, and $V_j(k)$ (i=1, . . . , $I_k$) is an estimated or known intermediate discharge voltage value ($V_\infty(k) < V_i(k) < V_0(k)$), and ho refers to a discharge holdoff time value;
    (5) providing measured values of a threshold discharge voltage value $V_\infty(meas)$, a prompt discharge voltage value $V_0(meas)$ and intermediate discharge voltage values $V_i(meas)$ (i=1, . . . , $I_k$), corresponding to the estimated or known threshold discharge voltage value, the estimated or known prompt discharge voltage value and the estimated or known intermediate discharge voltage values, respectively, for at least one candidate gas component, number k, of the gas G;
    (6) computing an error sum ε1(k) of weighted magnitudes of differences between (i-a) the estimated or known threshold discharge voltage value, (ii-a) the estimated or known prompt discharge voltage value and (iii-a) the estimated or known intermediate discharge voltage values, and the corresponding (i-b) measured threshold discharge voltage value, (ii-b) the measured prompt discharge voltage value and (iii-b) the measured intermediate discharge voltage values, respectively, for the at least one candidate gas component, number k;
    (7) when ε1(k) is no greater than a selected error threshold number ε1(k;thr) for at least one index number, k=k1, interpreting this condition as indicating that the candidate gas component number k=k1 is likely to be present in the gas G; and
    (8) when ε1(k) is greater than the selected error threshold number for all indices k, interpreting this condition as indicating that none of the candidate gas components is likely to be present in the gas G.

2. The method of claim 1, further comprising choosing said weighted error sum ε1(k) to be $$\varepsilon1(k; p1) = \sum_{i=1}^{I_k} w_i |V_i(k) - V_i(meas)|^{p1} + w_\infty |V_\infty(k) - V_\infty(meas)|^{p1} + w_0 |V_0(k) - V_0(meas)|^{p1},$$

where $w_i$, $w_0$ and $w_\infty$ are selected non-negative weight coefficients, at least one of $w_0$ and $w_\infty$ is positive, and p1=p1(k) is a selected positive exponent number.

3. The method of claim 1, further comprising obtaining at least one of said values $V_\infty(meas)$, $V_0(meas)$ and $V_i(meas)$ at a temperature no higher than about room temperature.

4. The method of claim 1, further comprising:
    measuring electrical current I(V) between said at least one CNT in said first array and said constant voltage plate, for at least first, second and third voltage differences V in a range $V_\infty < V$ between said at least one CNT and said constant voltage plate;
    determining a first rate of increase b1 of the electrical current I(V) with increase in the voltage V for V equal to a value V1 above but close to $V_\infty$;
    determining if a second rate of increase b2 exists for the electrical current I(V) with increase in the voltage V for V equal to a value V2 substantially greater than V1, where b2 is substantially greater than b1;
    where the rate b2 exists and is substantially greater than b1, interpreting this condition as indicating that said gas G has at least first and second distinct components.

5. The method of claim 4, further comprising interpreting said condition as indicating that said gas G has a second threshold discharge voltage value $V'_\infty$ that lies between said values V1 and V2.

6. The method of claim 1, wherein said process of providing at least one of said intermediate discharge voltage values $V_i(meas)$ comprises:
    providing a voltage difference ΔV between said first variable voltage source and said substantially constant voltage plate;
    beginning at a selected time, t=t1, rapidly increasing a magnitude of the voltage difference ΔV from 0 to a selected first positive voltage difference magnitude |ΔV₁|, and subsequently holding the voltage difference magnitude approximately constant;
    measuring an elapsed time Δt(|ΔV₁|), beginning at the time t=t1, at which a discharge of said gas G first occurs; and
    identifying a pair of values {ΔV₁, Δt(|ΔV₁|)} with at least one of said pairs $\{V_j(k), \Delta t(V_j(k);ho)\}_j$ of values of said discharge holdoff time Δt($V_j(k)$;ho) and a corresponding intermediate discharge voltage value $V_j(k)$, for at least one of said counting index values k.

7. A method for estimating a component of a gas, the method comprising:
    (1) providing a first array of spaced apart carbon nanotubes (CNTs) in a chamber, at least one CNT in the first array being attached at a first CNT end to a first variable voltage source and having a relatively sharp CNT tip at a second CNT end of the at least one CNT, where the second CNT end of the at least one CNT in the first array is spaced apart a distance d, in a range of about 10-200 µm, from a substantially constant voltage plate;

(2) providing a gas G, having at least one unknown gas component and having a pressure in a range of about $10^{-3}$–760 Torr, in the chamber;

(3) identifying K candidate gas components, numbered k=1, ..., K (K≧1) one or more of which may be present in the gas G;

(4) providing a collection of pairs of estimated or known discharge voltage values and corresponding discharge holdoff time values $\{V_j(k), \Delta t(V_j(k); ho)\}_j$ (j=0, 1, ..., $I_k$), for the candidate gas component number k, where $V_0(k)$ is an estimated or known prompt discharge voltage value, and $V_j(k)$ (i=1, ..., $I_k$) is an estimated or known intermediate discharge voltage value ($V_i(k) < V_0(k)$), and ho refers to a discharge holdoff time value;

(5) providing measured values of discharge holdoff times (i-a) for a prompt discharge holdoff time value $\Delta t(V_0(meas); ho)$ and (ii-a) for intermediate discharge holdoff time values $\Delta t(V_i(meas); ho)$ (i=1, ..., $I_k$) for the gas G, corresponding to (i-b) the estimated or known prompt discharge voltage value $\Delta t(V_0(k); ho)$, and (ii-b) the estimated or known intermediate discharge voltage values $\Delta t(V_i(k); ho)$, respectively, for the at least one candidate gas component, number k, of the gas G;

(6) computing an error sum ∈2(k) of weighted magnitudes of differences between the estimated or known discharge holdoff time values and the prompt discharge holdoff time value $\Delta t(V_0(k); ho)$ for the at least one gas component number k and the corresponding measured discharge holdoff time values and the prompt discharge holdoff time value $\Delta t(V_0(meas); ho)$ for the gas G, respectively;

(7) when ∈2(k) is no greater than a selected error threshold number ∈2(k;thr) for at least one index number k=k2, interpreting this condition as indicating that the candidate gas component number k=k2 is likely to be present in the gas G; and (8) when ∈2(k) is greater than the selected error threshold number for all indices k, interpreting this condition as indicating that none of the candidate gas components is likely to be present in the gas G.

8. The method of claim 7, further comprising choosing said weighted error sum ∈2(k) to be $$\varepsilon 2(k) = \sum_{i=0}^{I_k} w_i \left| \Delta t(V_i(k); ho) - \Delta t(V_i(meas); ho) \right|^{p2} +$$

$$w_0 \Delta t(V_0(k); ho) - \Delta t(V(meas); ho))^{p2},$$

where $w_i$ and $w_\infty$ are selected non-negative weight coefficients and p2=p2(k) is a selected positive exponent number.

9. The method of claim 7, further comprising obtaining at least one of said values $V_\infty(meas)$, $V_0(meas)$ and $V_i(meas)$ at a temperature no higher than about room temperature.

10. The method of claim 7, further comprising:
measuring electrical current I(V) between said at least one CNT in said first array and said constant voltage plate, for at least first, second and third voltage differences V in a range $V_\infty < V$ between said at least one CNT and said constant voltage plate;
determining a first rate of increase b1 of the electrical current I(V) with increase in the voltage V for V equal to a value V1 above but close to $V_\infty$;
determining if a second rate of increase b2 exists for the electrical current I(V) with increase in the voltage V for V equal to a value V2 substantially greater than V1, where b2 is substantially greater than b1;
where the rate b2 exists and is substantially greater than b1, interpreting this condition as indicating that said gas G has at least first and second distinct components.

11. The method of claim 10, further comprising interpreting said condition as indicating that said gas G has a second threshold discharge voltage value $V'_\infty$ that lies between said values V1 and V2.

12. The method of claim 7, wherein said process of providing at least one of said intermediate discharge voltage values $V_i(meas)$ comprises:
providing a voltage difference ΔV between said first variable voltage source and said substantially constant voltage plate;
beginning at a selected time, t=t1, rapidly increasing a magnitude of the voltage difference ΔV from 0 to a selected first positive voltage difference magnitude $|\Delta V_1|$, and subsequently holding the voltage difference magnitude approximately constant;
measuring an elapsed time $\Delta t(|\Delta V_1|)$, beginning at the time t=t1, at which a discharge of said gas G first occurs; and
identifying a pair of values $\{\Delta V_1, \Delta t(|\Delta V_1|)\}$ with at least one of said pairs $\{V_j(k), \Delta t(V_j(k); ho)\}_j$ of values of said discharge holdoff time $\Delta t(V_j(k); ho)$ and a corresponding intermediate discharge voltage value $V_j(k)$, for at least one of said counting index values k.

* * * * *